United States Patent [19]

Shih et al.

[11] Patent Number: 5,289,266

[45] Date of Patent: Feb. 22, 1994

[54] NONCONTACT, ON-LINE DETERMINATION OF PHOSPHATE LAYER THICKNESS AND COMPOSITION OF A PHOSPHATE COATED SURFACE

[75] Inventors: I-Fu Shih, Los Alamitos; David B. Chang, Tustin; Victor Vali, Laguna Hills, all of Calif.

[73] Assignee: Hughes Aircraft Company, Los Angeles, Calif.

[21] Appl. No.: 885,066

[22] Filed: May 14, 1992

Related U.S. Application Data

[63] Continuation of Ser. No. 666,541, Feb. 19, 1991, abandoned, which is a continuation of Ser. No. 393,198, Aug. 14, 1989, abandoned.

[51] Int. Cl.$^5$ .................. G01B 11/06; G01B 11/02
[52] U.S. Cl. .................. 356/382; 356/355; 356/357
[58] Field of Search .............. 356/381, 382, 445–448, 356/128, 132, 133, 135, 335–361; 427/9; 148/262; 423/305

[56] References Cited

U.S. PATENT DOCUMENTS

| | | | |
|---|---|---|---|
| 3,869,211 | 3/1975 | Watanabe et al. | 250/560 |
| 3,917,410 | 11/1975 | Ulrich | 356/128 |
| 4,072,422 | 2/1978 | Tanaka et al. | 356/361 |
| 4,129,781 | 12/1978 | Doyle . | |
| 4,189,335 | 2/1980 | Evans . | |
| 4,330,345 | 5/1982 | Miles et al. | 148/262 |
| 4,660,980 | 4/1987 | Takabayashi et al. | 356/357 |
| 4,707,611 | 11/1987 | Southwell | 356/382 |
| 4,748,329 | 5/1988 | Cielo et al. | 356/382 |
| 4,885,709 | 12/1989 | Edgar et al. | 356/382 |
| 4,895,444 | 1/1990 | Miyata et al. | 356/128 |
| 4,902,902 | 2/1990 | Tole | 356/382 |

FOREIGN PATENT DOCUMENTS 0163466 12/1985 European Pat. Off. .
0223485 5/1987 European Pat. Off. .
2589578 11/1985 France .

OTHER PUBLICATIONS

"Proceedings of the 1987 IEEE Int. Conference on Robotics and Automation", Aug. 1987, pp. 515–519; S. Parthasarathy et al.
*Transactions of the Institute of Metal Finishing*, vol. 61, 1983, pp. 155–160; M. O. W. Richardson et al.

*Primary Examiner*—Richard A. Rosenberger
*Assistant Examiner*—Hoa Q. Pham
*Attorney, Agent, or Firm*—Elizabeth E. Leitereg; Terje Gudmestad; W. K. Denson-Low

[57] ABSTRACT

A nondestructive method and apparatus is disclosed for determining the thickness and composition of a zinc phosphate layer applied to a metal surface, such as sheet metal on an automotive assembly line. The phosphate layer is irradiated with infrared light which is at least partially transmitted through the phosphate layer. Reflections from the upper and lower surfaces of the phosphate layer return a total reflected intensity which is a function of the optical parameters of the phosphate components and the ratio of the components corresponding to the optical parameters. In the event, for example, that a phosphate layer includes two zinc phosphate components, the measure of reflected intensity at two separate wavelengths will be different inasmuch as the optical properties of the zinc phosphate components is also a function of frequency. The measured reflected intensity and its functional dependence upon the ratio of the components within the phosphate layer can be taken together with the known values of the optical parameters of each component to compute the fraction of each component within the phosphate layer.

4 Claims, 2 Drawing Sheets

NONCONTACT, ON-LINE DETERMINATION OF PHOSPHATE LAYER THICKNESS AND COMPOSITION OF A PHOSPHATE COATED SURFACE

This is a continuation of application Ser. No. 07/666,541, filed Feb. 19, 1991, now abandoned, which is a continuation of application Ser. No. 393,198, filed Aug. 14, 1989, now abandoned.

BACKGROUND OF THE INVENTION

1. Field of the Invention

The invention relates to the field of nondestructive analysis of phosphate coated surfaces and in particular to the nondestructive determination of the thickness and composition of the phosphate layer of an automotive surface.

2. Description of the Prior Art

In recent years the cathodic electro-coating of paint primers onto phosphated steel has become increasingly important. This is particularly true in the automotive industry where the process is used as a precursor to undercoating and topcoating with acrylic base paints. In many instances the performance of the total corrosion resistance thus produced has been remarkably good, though particular care is required in selecting the correct phosphate system and application process. A particular example of such a phosphate coating for use in automotive paints is described in Richardson et al., "The Influence of Zinc Phosphate Crystalline Morphology on the Corrosion Resistance of Electro-Painted Steel", Transactions of the Institute of Metal Finishing, Volume 61, page 155 (1983).

Prior art methods for providing quality control of a phosphated steel surface comprised the steps of removing small chips of the phosphate coated surface from the automobile on the production line, transporting the chips to a laboratory, sometimes distantly separated from the assembly line, and then separating the phosphate layer from the substrate. The examination of the depth and composition of the layer was then made under a microscope with results reported back to the production line.

Clearly, with such prior art methods, even when the laboratory is located on site and at the immediate disposal of the quality control personnel on the manufacturing line, a substantial delay exists between the time when the sample is taken from the coated surface and when the results are reported. The cost and delay not only makes quality checking of each coated surface of an automobile impractical, but it tends to cause practical quality control by sampling techniques to be at best an after-the-fact determination. Depending upon the circumstances of manufacture, a corrective response cannot be made, (if one is indicated) on items being installed within assembled products. Correction can only be made to subsequently finished components. In the meantime, process variables may have changed and subsequent finished components may or may not continue to have the same defect or be defective to the same extent as the previously sampled product.

Therefore, what is needed is an on-line real-time nondestructive means for determining the thickness and composition of the phosphate layer on a steel surface.

BRIEF SUMMARY OF THE INVENTION

The phosphate material may be a blend of two components. Together they form a single layer of phosphate. The purpose of the invention is to provide an on-line non-contact method of measuring the thickness of the layer and determining the composition of the layer, i.e. ratio of one phosphate component to the other in the layer.

The invention is a method for nondestructively determining the thickness of the layer and the ratio of components included within a protective phosphate layer disposed on a substrate comprising the steps of illuminating the protective phosphate layer on the substrate with light of a first predetermined frequency. The intensity of reflected light from the protective phosphate layer is measured at the first frequency. The protective phosphate layer on the substrate is illuminated with light of a second predetermined frequency. The reflected light intensity from the protective phosphate layer is measured at the second frequency. The relative ratio of the first and second components and the thickness of the protective phosphate layer are determined from the measured intensities of reflected light from the protective phosphate layer at the first and second frequencies. The light at the first and second frequencies is reflected by the protective phosphate layer by means of the first and second surfaces of the protective phosphate layer. The protective phosphate layer is at least translucent to the light at the first and second frequencies.

As a result, the thickness and the relative ratio of the components within the protective phosphate layer are nondestructively determined.

In the preferred embodiment the first and second frequencies are unequal and are selected from the infrared spectrum. The measured reflected light is light reflected from at least two interfaces of the protective phosphate layer. The step of determining comprises the step of automatically computing the composition ratio of the components within the protective phosphate layer given the optical parameters at each predetermined frequency by utilizing the functional dependence of the reflected intensity upon the known optical parameters and the thickness.

In particular the phosphate layer has two components with effective fractional portions $\xi_1$ and $\xi_2$ with $\xi_1 + \xi_2 = 1$. The step of computing comprises the step of determining $d$, $\xi_1$ and $\xi_2$ corresponding respectively to the thickness of the layer and the fraction of each of the components of the protective phosphate layer respectively based upon measured reflective intensities at each frequency by the following equation:

$$I = a_0^2 [r_1^2 + (1-r_1)^4 r_2^2 e^{-4(\xi_1 \alpha_1 + \xi_2 \alpha_2)d \sec \phi'} + 2(1-r_1)^2 r_1 r_2 e^{-2(\xi_1 \alpha_1 + \xi_2 \alpha_2)d \sec \phi'} \cos 2(\xi_1 k_1 + \xi_2 k_2)d \cos \phi']$$

where I is the intensity of the reflected light;
- $a_0$ is the amplitude of light illuminating the substrate (and coating);
- $r_1$ is the reflectivity of the top surface of the phosphate film (i.e., phosphate/air interface);
- $r_2$ is the reflectivity of the phosphate/substrate interface;
- $\alpha_1$ is the absorptivity of the first component of the phosphate layer;
- $\alpha_2$ is the absorptivity of the second component of the phosphate layer;

$\xi_1$ is the fractional portion of the phosphate layer comprising the first component;

$\xi_2$ is the fractional portion of the phosphate layer comprising the second component;

$\phi'$ is the angle of refraction of the incident beam in the phosphate layer;

d is the thickness of the phosphate layer;

$k_1$ is the wave number of the illuminating radiation while inside the phosphate layer; and $k_2$ is the wave number.

The invention can be alternatively characterized as a method for nondestructively determining the actual thickness of a phosphate layer disposed upon a metal substrate for use in real-time nondestructive quality testing in an automotive assembly line comprising the steps of illuminating the phosphate layer with a light beam of a first frequency within the infrared spectrum. The first frequency is transmitted at least in part into the phosphate layer. The intensity of light reflected from the phosphate layer is measured at the first frequency. The phosphate layer is illuminated with a light beam of a second frequency within the infrared spectrum. The second frequency is transmitted at least in part into the phosphate layer. The intensity of light reflected from the phosphate layer is measured at the second frequency. The effective fractional portions $\xi_1$ and $\xi_2$ of the first and second phosphate components within the phosphate layer are automatically derived from the measured reflected intensities of light from the phosphate layer. The degree of reflected light from the phosphate layer is determined at least in part by the fraction of each phosphate component.

As a result, on-line, real-time quality control of painted metal surfaces in an automotive assembly line is performed.

In the illustrated embodiment the measured reflected light intensity is caused to be reflected by the front and the back surfaces of the phosphate layer.

The method further comprises illuminating the phosphate layer at additional frequencies. The number of the additional frequencies equals the number of additional phosphate components contained within the phosphate layer. The intensity of reflected light from the phosphate layer is measured at the additional frequencies. The fraction of each phosphate component within the phosphate layer is automatically derived based upon the measured intensities of reflected light at each of the frequencies including the additional frequencies.

The invention is still further characterized as an improvement in an apparatus for determining composition and thickness of a phosphate layer on sheet metal on a real-time basis in an automotive production line comprising a coherent light source for illuminating the phosphate layer with light at a plurality of frequencies. The phosphate layer is at least partially translucent to the light at each of the frequencies. A light detector measures the intensity of reflected light from the phosphate layer at each of the frequencies. A computer automatically derives the fraction of each of the components contained within the phosphate layer causing the light to be reflected from the phosphate layer.

As a result, real-time nondestructive quality control of the phosphate layer is performed.

The coherent light source for illuminating the phosphate layer and light detector for measuring the intensity of the light reflected from the phosphate layer provides and measures as many frequencies respectively as there are components within the phosphate layer.

DETAILED DESCRIPTION OF THE PREFERRED EMBODIMENT

A nondestructive method and apparatus is disclosed for determining the fractional partion of each zinc phosphate component within a phosphate layer applied to a metal surface, such as phosphate sheet metal within an automotive assembly line. The phosphated layer is irradiated with infrared light which is at least partially transmitted through the phosphate layer. Reflections from the upper and lower surfaces of the phosphate layer return a total reflected intensity which is a function of the optical parameters (e.g., reflectivity, absorptivity and index of refraction) of the phosphate layers and the fractional partions of the components corresponding to the optical parameters. In the event, for example, that a phosphate layer includes two zinc phosphate components, the measure of reflected intensity at two separate wavelengths will be different inasmuch as the optical properties of the zinc phosphate components is also a function of wavelength. The measured reflected intensity and its functional dependence upon the relative ratio of the components within the phosphate layer can be taken together with the known values of the optical parameters of each component to compute the fractional partion of each component within the phosphate layer.

The present invention provides a methodology and means to determine the actual thickness and composition of a phosphate layer on a steel or metal substrate. Interferometric data at two selected wavelengths is recorded. The data is input into a theoretical model and the fractional portion of each component of the phosphate layer is determined. A weighted ratio of various phosphate components within the phosphate layer is also determined.

In the illustrated embodiment, the phosphate components include zinc phosphate, $Zn_3(H_3PO_4)_2$, and zinc ferrous phosphate, $Zn_2Fe(H_3PO_4)_2$. These components may have a blurred interface between them, or may comprise a nonuniform or even a homogeneous mixture of the two components.

Figure 1:
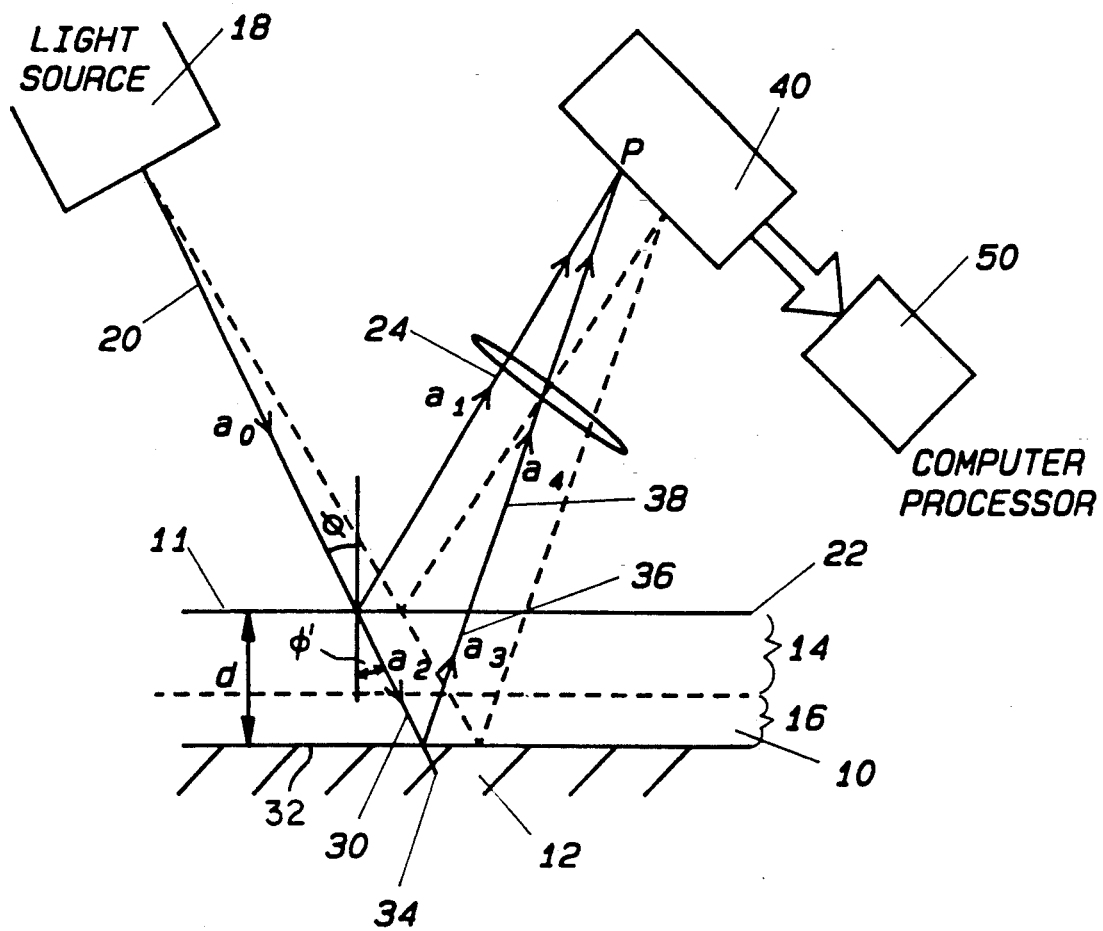
FIG. 1 is a highly diagrammatic depiction of the measurement apparatus shown optically measuring the thickness of a phosphate layer, shown in cross section in greatly exaggerated scale.

Turn now to FIG. 1 wherein the illustrated embodiment is conceptually described. A phosphate layer 10 is disposed on a steel substrate 12, typically a sheet metal component of an automobile or other vehicle. Phosphate layer 10 is idealized in FIG. 1 as being comprised of a first phosphate component or layer 14 and a second underlying phosphate component 16 in contact with steel substrate 12. A coherent light source 18, such as a laser operating at 10.6 micrometers, illuminates surface 11 with a beam 20 of amplitude $a_0$ oriented at an angle $\phi$ with respect to a line drawn perpendicular to the surface of substrate 12.

However, the wavelength of the incident beam 20 is chosen at a portion of the spectrum wherein phosphate layer 10 is at least semitransparent or translucent. While phosphate layers 10 may be opaque in the visible spectrum, in the infrared spectrum such as shown in FIG. 2, a wavelength, range of wavelengths or multiple range of wavelengths will exist wherein the phosphate layer will be semitransparent.

Figure 2:
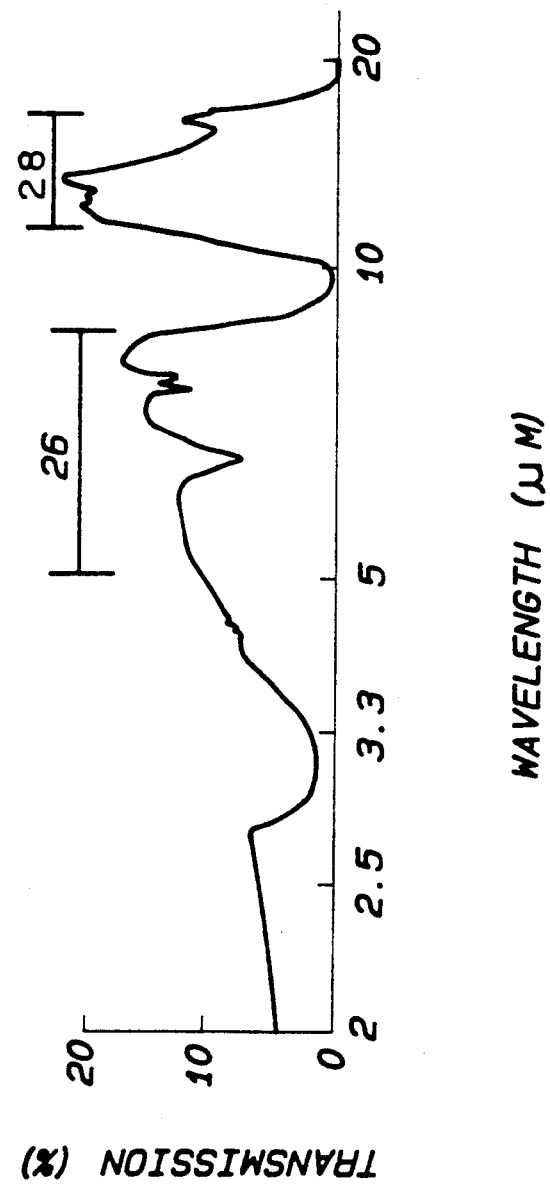
FIG. 2 is a graph of a typical infrared transmission spectrum for a phosphate compound used in phosphate coating of a metal surface.

For example, turning to FIG. 2, the transmission spectrum of a typical phosphate layer is graphically illustrated. The vertical axis represents the percentage transmission of the incident beam across an interface, while the horizontal axis represents the wavelength in microns. Inspection of the transmission spectrum of FIG. 2 readily indicates that there are two wavelength ranges in which good transmissivity is obtained through the interface, namely the wavelength ranges referenced by numerals 26 and 28. The peak in range 28 is in fact in excess of 20% and could be chosen as one frequency for coherent light source 18. A nearby distinguishable frequency on the same peak could be chosen as the second frequency, or one of the peaks within range 26 could alternately be chosen to designate a second wavelength of coherent light source 18 usable according to the invention as described below.

It must be clearly understood that the transmission spectrum shown in FIG. 2 is illustrated by way of example only. The transmission spectra of any particular phosphate can be empirically measured and two appropriate frequencies for transmission therethrough determined according to the teachings of the invention.

Turning now to FIG. 1, incident beam 20, with amplitude is partially reflected in ray 24 with amplitude $a_1$ and partially transmitted as ray 30 with amplitude $a_2$. Ray 30 travels through the combined thickness of phosphate layers 14 and 16 and is incident on the phosphate-to-metal interface 32. A portion of ray 30 will again be transmitted into metal substrate 12 as ray 34 with a greater portion being reflected back upwardly through phosphate layer 10 as ray 36 with an amplitude $a_3$. Ray 36 is incident on the underside of interface 22 and a portion again will be transmitted therethrough as ray 38 with an amplitude $a_4$. Rays 24 and 38 for each incident beam 20 will constructively or destructively combine to form an interfering fringe pattern which can be focused on a photographic plate, light detector or video camera 40. As will be shown below, the intensity of the reflected light is measured and the thickness of phosphate layer 10 determined, for example by a computer 50 programmed to solve the various equations given below.

Treating the amplitudes of the waves as complex numbers bearing phase information, the incident amplitude received by detector 40 is the sum of rays 24 and 38, namely $$a = a_1 + a_4 \tag{1}$$

where
- a = amplitude at detector 40
- $a_1$ = amplitude reflected from interface 22
- $a_4$ = amplitude transmitted through interface 22 after reflected from interface 32.

The values for amplitudes $a_1$ and $a_4$ can be rewritten in terms of: 1) the incident amplitude $a_0$; 2) the reflectivity of interface 22 and 32, designated as $r_1$ and $r_2$ respectively; 3) the absorptivity, $\alpha$, of phosphate layer 10; 4) k, the wave number of the radiation while inside phosphate layer 10; and 5) the thickness, d, of phosphate layer 10. The detected amplitude, a, is therefore set forth as shown below in Equation 2.

$$a = a_0[r_1 + (1-r_1)^2 r_2 e^{-2\alpha d \sec \phi} e^{2ikd \cos \phi}] \tag{2}$$

where
- $r_1$ = reflectivity of interface 22
- $r_2$ = reflectivity of interface 32
- $\alpha$ = absorptivity of layer 10
- k = wave number in layer 10
- $\phi$ is the angle the incident beam makes with respect to the normal to the surface.

The intensity of the observed beam at detector 40 is the absolute magnitude squared of the detected amplitude given in Equation 2 above. Therefore, the intensity of the detected beam reflected from phosphate layer 10 on metal substrate 12 is given below in Equation 3.

$$I = |a|^2 = a_0^2[r_1^2 + (1-r_1)^4 r_2^2 e^{-4\alpha d \sec \phi'} + 2(1-r_1)^2 r_1 r_2 e^{-2\alpha d \sec \phi'} \cos(2kd \cos \phi')] \tag{3}$$

where $\phi'$ is the refracted beam angle inside the phosphate layer, which is related to $\phi$ by $n \sin \phi' = \sin \phi$, where n is the index of refraction.

The intensity is thus a function of the optical parameters (absorptivity, reflectivity and index of refraction) of phosphate layer 10 and the thickness d of the layer. The intensity varies periodically as a function of $\phi$ or $\phi'$ because of the term, cos (2kd cos $\phi'$). The intensity is thus a maximum when 2kd cos $\phi' = 0, 2\pi, 4\pi, \ldots$ and is a minimum at 2kd cos $\phi' = \pi, 3\pi, 5\pi, \ldots$ By measuring the periodicity of the fringes in the image plane and noting that $\Delta x = f \Delta \phi$ where f is the focal length of the lens, d can be determined.

However, in reality phosphate layer 10 is in fact a composite layer of either two separate components, two separate component layers which are merged with partial overlap, or a nonuniform or homogeneous mixture of two layers with each other with no clear interface between the internal layers within layer 10. Each phosphate component within layer 10 will contribute to the optical properties of layer 10. Thus, the absorptivity and wave number of the radiation within layer 10 as expressed in the above equations may be regarded as an average from both phosphate components within layer 10 weighted by the proportion of each phosphate component within the layer. Therefore, the weighted averages of the quantities, $<\alpha>$, $<d>$ and $<kd>$ which appears in Equation 3 can be considered as given by the following Equation 4.

$$<\alpha> = \xi_1 \alpha_1 + \xi_2 \alpha_2$$

$$<k> = \xi_1 k_1 + \xi_2 k_2 \tag{4}$$

where
- $\alpha_1$ is absorptivity of the first phosphate
- $\xi_1$ is the fractional portion of the phosphate layer comprising the first phosphate component
- $\alpha_2$ is the absorptivity of the second phosphate component
- $\xi_2$ in the fractional portion of the phosphate layer comprised of the second phosphate component with $\xi_1 + \xi_2 = 1$.

Substituting the values for $<\alpha>$ and $<k>$ from Equation 4 into Equation 3 we obtain the following result $$I = a_0^2[r_1^2 + (1-r_1)^4 r_2^2 e^{-4(\xi_1 \alpha_1 + \xi_2 \alpha_2) d \sec \phi'} + 2(1-r_1)^2 r_1 r_2 e^{-2(\xi_1 \alpha_1 + \xi_2 \alpha_2) d \sec \phi'} \cos 2(\xi_1 k_1 + \xi_2 k_2) d \cos \phi']$$

Therefore the intensity of the measured beam is a function of known constants and the fractional portions, $\xi_1$ and $\xi_2$, of the two phosphate components within phosphate layer 10. By measuring the intensity at two separate wavelengths, the optical constants being separately known at each wavelength, we can then obtain two equations of the form set forth above with two unknowns. Although not linear equations, by noting that $\xi_1 = 1 - \xi_2$, measuring the fringe period for d at two different wavelengths, the two equations can be numerically solved, e.g. by a computer 50, to provide values for $\xi_1$ and $\xi_2$. Thus, an on-line and real time determination of the thickness and composition of the phosphate layer is made.

If more than two phosphate components are present, then the procedure may be repeated with as many additional wavelengths as there are phosphate components for which effective aggregate thicknesses are to be obtained. Being able to determine each of these fractional portions then allows a practitioner to have a quantitative understanding of how the phosphate components are distributed within the layer and whether the beneficial corrosion resistance effects achievable in theory from such phosphate layers are likely to be realized. Of course for more than two components, $\xi_1 + \xi_2 + \xi_3 + \cdots = 1$.

The illustrated embodiment has been set forth solely as an example and should not be taken as limiting the invention which is defined by the following claims. It is to be understood that many alterations and modifications may be made by those of ordinary skill in the art without departing from the spirit and scope of the invention.

We claim:

1. A method for nondestructively determining the thickness and the fractional portions of a first and a second phosphate component of a protective phosphate layer disposed on a substrate comprising the steps of:

illuminating said protective phosphate layer on said substrate with an incident beam of light of a first predetermined frequency, measuring the intensity of reflected light from said protective phosphate layer at said first frequency;

illuminating said protective phosphate layer on said substrate with light of a second predetermined frequency;

measuring reflected light intensity from said protective phosphate layer at said second frequency; and determining the fractional portions of a first and second component of said protective phosphate layer from said measured intensities of reflected light from said protective phosphate layer at said first and second frequencies, said light at said first and second frequencies being reflected by said protective phosphate layer by means of first and second interfaces of said protective phosphate layer, said protective phosphate layer being at least translucent to said light at said first and second frequencies, said step of determining comprising:

automatically computing said fractional portion of each said component within said protective phosphate layer based on known optical parameters at each said predetermined frequency as known by utilizing a functional dependence of said intensity of reflected light upon said known optical parameters and said thickness, whereby the fractional portions of each of said components within said protective phosphate layer is nondestructively determined, and wherein said phosphate layer has at least two components of fractional portions $\xi_1$ and $\xi_2$ respectively, where said step of computing comprises the step of determining $\xi_1$ and $\xi_2$ based upon measured reflected light intensities at each said frequency, by the following equation:

$$I = a_0^2 [r_1^2 + (1-r_1)^4 r_2^2 e^{-4(\xi_1 \alpha_1 + \xi_2 \alpha_2)d \sec \phi'} \\ + 2(1-r_1)^2 r_1 r_2 e^{-2(\xi_1 \alpha_1 + \xi_2 \alpha_2)d \sec \phi'} \\ \cos 2(\xi_1 k_1 + \xi_2 k_2) d \cos \phi']$$

where for each said predetermined frequency:

I is the intensity of said measured reflected light at said predetermined frequency, $a_0$ is the amplitude of light illuminating said substrate, $r_1$ is the reflectivity of a first top interface of said phosphate layer, $r_2$ is the reflectivity of a second bottom interface of said phosphate layer, $\alpha_1$ is the absorptivity of said first component of said phosphate layer, $\alpha_2$ is the absorptivity of said second component of said phosphate layer, $\xi_1$ is the fractional portion of said first component of said phosphate layer, $\xi_2$ is the fractional portion of said second component of said phosphate layer, and $\phi'$ is the angle of refraction of the incident beam in said phosphate layer with respect to the surface normal of said phosphate layer.

2. A method for nondestructively determining the thickness of a protective phosphate layer disposed on a substrate comprising the steps of:

illuminating said protective phosphate layer on said substrate with an incident beam of light of a first predetermined frequency, said protective phosphate layer being at least translucent to said light beam at said first frequency such that said light beam is transmitted through and reflected from a first surface of said layer and transmitted through and reflected from a second surface of said layer, said layer having absorptivity and an index of refraction;

measuring the intensity of reflected light from said protective phosphate layer at said first frequency from said first surface and said second surface;

illuminating said protective phosphate layer on said substrate with light of a second predetermined frequency, which is different from said first frequency, said protective phosphate layer being at least translucent to said light beam at said second frequency such that said light is transmitted through and reflected from said first surface of said layer and transmitted through and reflected from said second surface of said layer;

measuring the intensity of reflected light from said protective phosphate layer at said second frequency from said first surface and said second surface; and determining the thickness of said protective phosphate layer from the measured intensity of reflected light, which is a function of reflectivity from said first and said second surfaces, an angle of refraction of said transmitted light through said first surface; wave number of said light while inside said protective phosphate layer and absorptivity of said protective phosphate layer, wherein the step of determining comprising determining said thickness from the following equation:

$$I = a_0^2[r_1^2 + (1-r_1)^4 r_2^2 e^{-4\alpha d \sec\phi'} + 2(1-r_1)^2 r_1 r_2 e^{-2\alpha d \sec\phi'} \cos(2kd \cos\phi')],$$

where
$a_0$ is an incident amplitude of said light,
$r_1$ is a reflectivity from said first surface,
$r_2$ is a reflectivity from said second surface,
$\alpha$ is the absorptivity of said layer,
$k$ is a wave number of said light while inside said layer,
$\phi'$ is a refracted light beam angle of said transmitted light through said first surface, and
$d$ is the thickness of said layer.

3. A method of nondestructively determining the fractional portions of a first phosphate component and a second phosphate component of a protective phosphate layer disposed on a substrate comprising the steps of:
illuminating said protective phosphate layer on said substrate with an incident beam of light of a first predetermined frequency, said protective phosphate layer being at least translucent to said light beam at said first frequency such that said light beam is transmitted through and reflected from a first surface of said layer and transmitted through and reflected from a second surface of said layer, said layer having an average absorptivity and wave number which are weighted by the proportion of each phosphate component within said layer;
measuring the intensity of reflected light from said protective phosphate layer at said first frequency from said first surface and said second surface;
illuminating said protective phosphate layer on said substrate with a light beam of a second predetermined frequency, which is different from said first frequency, said protective phosphate layer being at least translucent to said light beam at said second frequency such that said light beam is transmitted through and reflected from said first surface of said layer and transmitted through and reflected from said second surface of said layer;
measuring the intensity of reflected light from said protective phosphate layer at said second frequency from said first surface and said second surface; and
determining the fractional portions of said first and said second phosphate components from the measured intensity of reflected light at each said predetermined frequency, which is a function of said layer thickness, reflectivity from said first and said second surfaces, absorptivity of said first and said second components, wave number of said light while inside said first and said second components and an angle of refraction through said first surface, wherein the step of determining comprises determining said fractional portions from the following equation:

$$I = a_0^2[r_1^2 + (1-r_1)^4 r_2^2 e^{-4(\xi_1\alpha_1 + \xi_2\alpha_2)d \sec\phi'} + 2(1-r_1)^2 r_1 r_2 e^{-2(\xi_1\alpha_1 + \xi_2\alpha_2)d \sec\phi'} \cos 2(\xi_1 k_1 + \xi_2 k_2)d \cos\phi']$$

where for each said predetermined frequency:
$I$ is the intensity of said measured reflected light at said predetermined frequency,
$a_0$ is an amplitude of light illuminating said substrate,
$r_1$ is a reflectivity of a first top interface of said phosphate layer,
$r_2$ is a reflectivity of a second bottom interface of said phosphate layer,
$\alpha_1$ is an absorptivity of said first component of said phosphate layer,
$\alpha_2$ is an absorptivity of said second component of said phosphate layer,
$k_1$ is a wave number of said first component of said phosphate layer,
$k_2$ is a wave number of said second component of said phosphate layer,
$\xi_1$ is the fractional portion of said first component of said phosphate layer,
$\xi_2$ is the fractional portion of said second component of said phosphate layer and $\xi_1 + \xi_2 = 1$,
$d$ is the thickness of said protective phosphate layer, and
$\phi'$ is an angle of refraction of the incident beam in said phosphate layer with respect to the surface normal of said phosphate layer.

4. A method for determining the thickness or composition of a layer of material, said layer having N components and having a top and bottom surface which define first and second interfaces, respectively, said method comprising the steps of:
a) illuminating said layer with light at N different predetermined frequencies, said layer being at least translucent to light at each of said N frequencies and being reflective of light at said N frequencies at each of said interfaces;
b) measuring the intensity of light reflected from said interfaces at said N frequencies; and
c) determining the thickness or fractional portions of said layer from said measured reflected intensity at each said N different predetermined frequencies, which is a function of reflectivity at a first top interface and a second bottom interface of said phosphate layer, a weighted average absorptivity of said phosphate layer, a weighted average wave number of said light while inside said phosphate layer, and an angle of refraction of light through said first top interface, wherein said step of determining comprises determining said thickness or fractional portions from an equation:

$$I = a_0^2[r_1^2 + (1-r_1)^4 r_2^2 e^{-4<\alpha>d\sec\phi'} + 2(1-r_1)^2 r_1 r_2 e^{-2<\alpha>d\sec\phi'} \cos(2<k>d\cos\phi')],$$

where for each said predetermined frequency:
$I$ is the intensity of said measured reflected light at said predetermined frequency,
$a_0$ is an amplitude of light illuminating said substrate,
$r_1$ is said reflectivity of said first top interface of said phosphate layer,
$r_2$ is said reflectivity of said second bottom interface of said phosphate layer,
$<\alpha>$ is said weighted average absorptivity of said layer,
$<k>$ is said weighted average wave number of said light while inside said layer, $\phi'$ is said refracted light beam angle of said transmitted light through said first top interface, and d is the thickness of said layer, wherein:

$$<\alpha> = \xi_1\alpha_1 + \xi_2\alpha_2 + \xi_3\alpha_3 + \ldots \xi_N\alpha_N, \text{ and}$$

$$<k> = \xi_1 k_1 + \xi_2 k_2 + \xi_3 k_3 + \ldots \xi_N k_N,$$

and wherein:

$\alpha_1, \alpha_2, \alpha_3 \ldots \alpha_N$ are absorptivities of said N components of said phosphate layer, $k_1, k_2, k_3, \ldots k_N$ are wave numbers of light while inside said N components of said phosphate layer, $\xi_1, \xi_2, \xi_3 \ldots \xi_N$ are fractional portions of said N components of said phosphate layer and $\xi_1 + \xi_2 + \xi_3 + \ldots \xi_N = 1$ and N is equal to or greater than 1.

* * * * *